US012740878B2

(12) United States Patent
Frid et al.

(10) Patent No.: US 12,740,878 B2
(45) Date of Patent: Sep. 22, 2026

(54) CEREBRAL STENT

(71) Applicant: INTRESSA VASCULAR S.A., Isnes (BE)

(72) Inventors: Noureddine Frid, Beersel (BE); Eric Marcoux, Wemmel (BE)

(73) Assignee: INTRESSA VASCULAR S.A., Isnes (BE)

( * ) Notice: Subject to any disclaimer, the term of this patent is extended or adjusted under 35 U.S.C. 154(b) by 533 days.

(21) Appl. No.: 18/263,284

(22) PCT Filed: Jan. 31, 2022

(86) PCT No.: PCT/EP2022/052209
§ 371 (c)(1),
(2) Date: Jul. 27, 2023

(87) PCT Pub. No.: WO2022/162219
PCT Pub. Date: Aug. 4, 2022

(65) Prior Publication Data

US 2024/0082025 A1 Mar. 14, 2024

(30) Foreign Application Priority Data

Feb. 1, 2021 (EP) .................................... 21154577

(51) Int. Cl.
*A61F 2/90* (2013.01)
*A61F 2/82* (2013.01)

(52) U.S. Cl.
CPC .......... *A61F 2/90* (2013.01); *A61F 2002/823* (2013.01); *A61F 2210/0076* (2013.01)

(58) Field of Classification Search
CPC ................................................ A61F 2002/823
See application file for complete search history.

(56) References Cited

U.S. PATENT DOCUMENTS 4,655,771 A 4/1987 Wallsten
2007/0162104 A1* 7/2007 Frid .......................... A61F 2/90
623/1.53

(Continued)

OTHER PUBLICATIONS

International Search Report and Written Opinion of the International Searching Authority from the European Patent Office, in PCT/EP2022/052209 dated Apr. 19, 2022, which is an international application to which this application claims priority.

*Primary Examiner* — Tuan V Nguyen
(74) *Attorney, Agent, or Firm* — Kolitch Romano Dascenzo Gates LLP

(57) ABSTRACT

An implantable endoluminal prosthesis is described for use in the treatment of aneurysm involving branches. The prosthesis has a multilayer configuration, including a self-expandable braided framework extending along an axis and able to expand from a radially compressed state in a delivery configuration to a radially expanded state. The self-expandable braided framework is formed by wires, is devoid of any impermeable cover layer, includes a plurality of layers of wires made of biocompatible material, and forms a wall of the endoluminal prosthesis. Each layer forms a mesh, the meshes forming a lattice and being interlocked, the wires being integrated in the mesh of at least one of the adjacent layers. The self-expandable braided framework has a cylindrical lumen. The ratio of the surface coverage ratio of the outer layer to the surface coverage ratio of the inner layer is at least 1.5.

12 Claims, 6 Drawing Sheets

(56) References Cited

U.S. PATENT DOCUMENTS

| | | | | |
|---|---|---|---|---|
| 2009/0192587 | A1 | 7/2009 | Frid | |
| 2013/0218255 | A1 * | 8/2013 | Cattaneo .................. | A61F 2/90 623/1.11 |
| 2015/0238333 | A1 | 8/2015 | Berez et al. | |
| 2018/0311056 | A1 | 11/2018 | Pung et al. | |

* cited by examiner (a) (b) (c) (d)

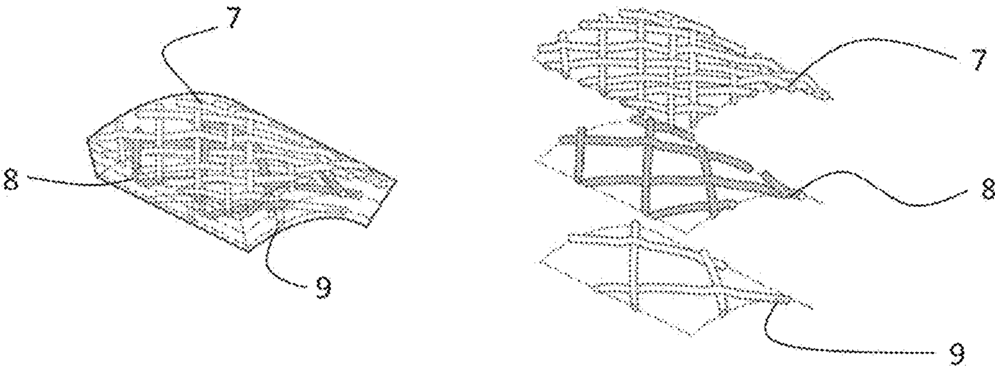
Figure 7
Figure 8
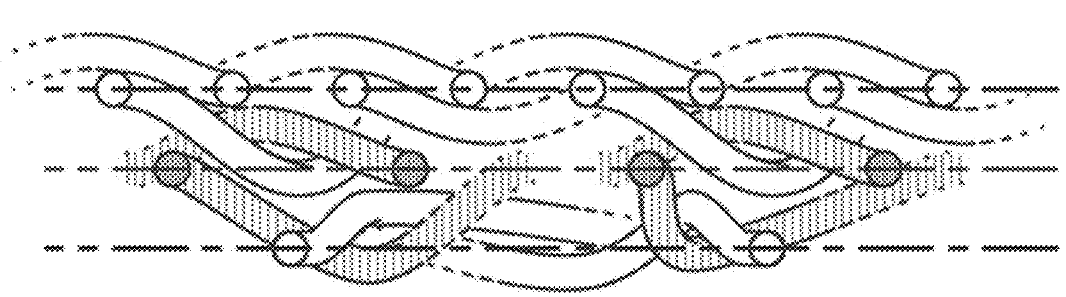
Figure 9

CEREBRAL STENT

TECHNICAL FIELD

The present disclosure is related to a multilayer endovascular prosthesis (stent).

BACKGROUND ART

The cerebro-vasculature, in addition to supplying nutrients and other essential molecules, is a key component of the blood-brain barrier (BBB), which maintains tight control of the brain microenvironment by regulating fluctuations in chemistry, transport of immune cells, and the entry of toxins and pathogens.

To reach any part of the brain, the blood supply articulates on three stages:

1) The Arterial Blood Supply

Four principal arteries supply the brain, namely one internal carotid artery (ICA) and one vertebral artery (VA) on each side. Classically the internal carotid arteries on both sides are referred to as the anterior circulation, while the vertebral-basilar arterial system composes the posterior circulation.

2) The Microvasculature Blood Supply

The cardiovascular system is composed of successive generations of these vascular branching's, from level 0 (carotids) to level N (the capillaries and arterioles). Capillaries and arterioles regulate vascular pressures and microvascular resistance. A constant "conflict" exists between preserving arterial pressure by increasing arteriolar resistance and allowing all regions to receive sufficient perfusion to provide oxygen to the tissue. The decrease of the resistance in small vessels should maintain the equilibrium of oxygen perfusion with sufficient resistance to maintain the system blood pressure from falling. Following the literature, the normal pressure in an arteriole is typically 30 to 70 mmHg, while the pressure in a venule is 10 to 16 mmHg. On the other hands, large arteries are simply conduits to allow blood transfer between locations. These large vessels have very low resistance and do not play a significant role in pressure regulation. Small arteries (0.5 to 1 mm in diameter) control 30 to 40 percent of total vascular resistance, and arterioles (500 μm in diameter) combined with those small arteries make up 70 to 80 percent of total vascular resistance. Nearly 20 to 30 percent of the resistance comes from capillaries and venules 3) Perforators Hemodynamics Perforators are micro-vessels arising from large cerebral arteries. They are close to or from the terminal divisions, the branching sites, or the parent arteries' junctions, where saccular aneurysms most often develop (see FIG. 3). The perforators are the parent artery to micro-vascular network that is consisting of bifurcated fractal tree where the flow is distributed as uniformly as possible in order to achieve an efficient transport system.

The branching's or bifurcations can cause the flow to loose certain amount of flow during the process of flow division at the bifurcation. At low Re number (Reynolds number) from which no vortex is produced, increment in bifurcation angle causes the increase of stagnation effect, and eventually recover the normal speed away from bifurcation.

The microvascular network consisted of a bifurcating fractal tree where the flow is distributed as uniformly as possible in order to achieve an efficient transport system. In this sense, the development of uniform velocity profile after the bifurcation at low Re effectively minimizes the loss of transport efficiency in the flow.

In the other hand, the pathological change caused by the aneurysm modifies the flow environment around, particularly through the perforators. This situation seems to cause flow stagnation at the branching level even at low Re number. The flow disturbance may induce stenosis that can affect the blood distribution through the whole microvessels tree or can cause thrombosis in perforators and capillaries. The loss of stability and a lack of flow to a single simple penetrating vessel inevitably lead to cortical damage, and lacunar infarcts (small infarcts). Lacunar infarcts are asymptomatic that are often seen in association with micro-bleeds and deterioration.

4) Monolayer Braided Wire Mesh

Braided wire mesh, as described by U.S. Pat. No. 4,655,771, is commonly used to disrupt, to reduce the flow in the aneurysmal sac, and consequently to promote clot that excludes the aneurysm from the circulation. In other words, this type of mesh, as described is a monolayer braid that is used to divert the flow but doesn't change, effectively, its turbulent flow pattern.

To be effective, the braided wire meshes, following U.S. Pat. No. 4,655,771, that are used to treat the cerebral aneurysms must have a low porosity or high mesh density. To obtain this desired parameter, the axially directed angle between crossing elements is high obtuse angle around 140 degrees at radially unloaded conditions.

Ideally, the main goal of this monolayer device is to create an intra-saccular hemodynamic environment that induces organized and stable thrombus formation as well as to promote endothelialization, reconstruction of the parent artery and maintain adequate flow jailed side branches.

The less porous the structure is, the greater the intra-saccular hemodynamic is considered to be effective but greater is the risk of perforators occlusion.

The main concerns with this type of devices include:

- complications associated with delayed bleeding after treatment, possibly associated to unstable or disorganized thrombosis and lack of protection of the aneurysm wall for a prolonged period;
- complications associated to the anticoagulation regime prescribed to prevent in-device thrombosis;
- complications associated to in-stent stenosis or thrombosis;
- complications associated to the occlusion of perforators or other arteries jailed by the devices.

The monolayer mesh design is defined by a limited number of pores that can affect the flow rate through a branch. These pores number cannot allow more flow than its physical capacity.

An example is given to emphasize the limitation of the flow: if we consider taking a 2D piece sheet metal, and drilling a whole through it. Fluid will flow through this pore at low rate. To double the flow rate, one more hole with same size is needed to double the flow rate. Drilling more holes throughout the entire surface of the metal sheet will continue to increase the flow rate until there is no room for more holes. The same would be true for a 2-D braided metal with uniform holes throughout, as described by the U.S. Pat. No. 4,655,771.

When the flow bifurcates to the perforator, it loses a certain amount of the flow velocity and consequently energy, which recirculates at the entrance region, as described earlier. Due to the designed limitation mentioned above, the monolayer device does not help to improve velocity profile in the perforator jailed thereby because it increases the flow resistance.

The flow stagnation at the entrance region of the perforator may lead to a stenosis or occlusion. The literature estimates the perforator occlusion rate at 13%.

SUMMARY

The present disclosure is related to a cerebral implantable endoluminal prosthesis for use in the treatment of cerebral aneurysm involving branches having a multilayer configuration, comprising at least one self-expandable braided framework extending along an axis able to expand from a radially compressed state in a delivery configuration to a radially expanded state; the self-expandable braided framework being formed by wires; this self-expandable braided framework devoid of any impermeable cover layer, comprising a plurality of layers of wires made of biocompatible material and forming a wall of the endoluminal prosthesis; each layer forming a mesh; the meshes forming a lattice with a plurality of wires of said layers; the meshes being interlocked, the wires being integrated in the mesh of at least one of the adjacent layers; the self-expandable braided framework comprising a lumen in a cylindrical form with a circular cross-section and a constant diameter; characterized in that, the different layers of the plurality of layers have different surface coverage ratio, the ratio of the surface coverage ratio of the outer layer to the surface coverage ratio of the inner layer being at least 1.5.

Said differently, the number of wires crossing a line parallel to the lumen axis in a given layer is higher in the outermost layer than in the innermost layer. Preferably, the ratio of the number of wires in the outermost layer to the innermost layer is at least 1.5, preferably at least 2.

Preferably, the number of wires forming the endoluminal prosthesis is comprised at least 50, preferably at least 80, even more preferably at least 90. Advantageously, the number of wires is at most 120, more preferably at most 102.

Advantageously, the endoluminal prosthesis of the present disclosure is particularly adapted to cerebral application with nominal diameter (diameter without external constraint) comprised between 3 and 5.5 mm.

Preferably, the wires forming the endoluminal prosthesis have a diameter comprised between 10 and 70 μm, preferably between 20 and 50 μm, even more preferably between 30 and 40 μm.

Advantageously, all wires have the same diameter.

Advantageously, the ratio of the surface coverage ratio of the outer layer to the surface coverage ratio of the inner layer being at least 2.

Preferably, the implantable endoluminal prosthesis comprises at least three layers, the intermediate layer(s) having a surface coverage ratio comprised between the surface coverage ratio of the inner layer and the surface coverage ratio of the outer layer. Said differently, the number of wires in the intermediate layer is comprised between the number of wires in the outermost layer and the number of wires in the innermost layer.

Advantageously, the biocompatible material of the implantable endoluminal prosthesis comprises a metallic substrate selected from the group consisting of titanium, nickel-titanium alloys such as nitinol and Nitinol-DFT®-Platinum, any type of stainless steels, or a cobalt-chromium-nickel alloys such as Phynox®.

BRIEF DESCRIPTION OF THE DRAWINGS

FIG. 7. shows 3 interlaced layers with 3 different degrees of porosity

FIG. 8. shows a schematic cross section view of 3 interlaced layers with 3 different degrees of porosity.

FIG. 9 represents a plan view of 3 interlaced (or interlocked or interbraided) layers with 3 different degrees of porosity (i.e. wire densities).

FIGURE KEYS

Figure 1:
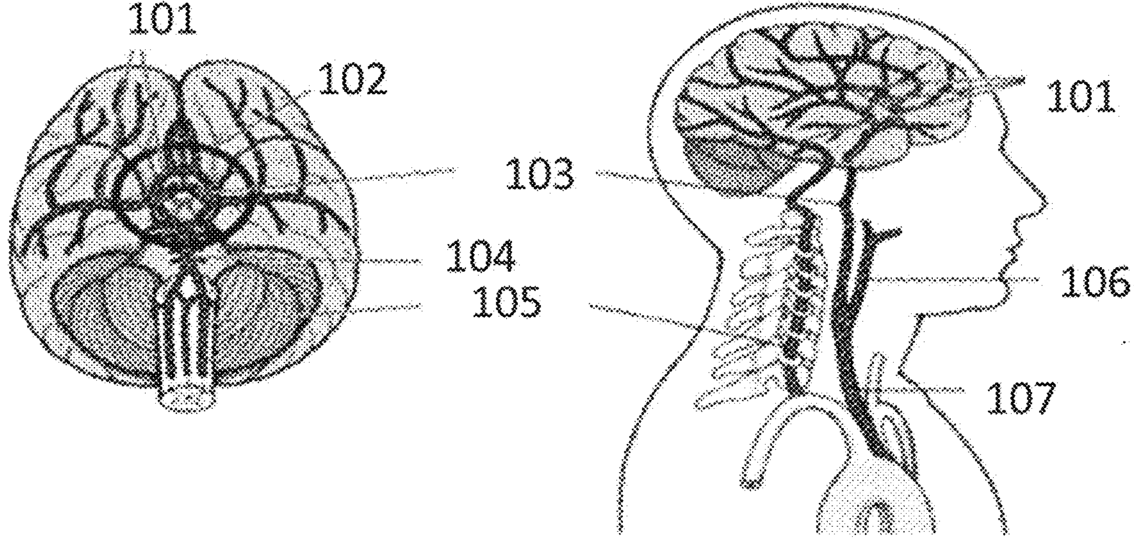
FIG. 1. Schematically shows the vertebral artery feeding the posterior part of the brain and the carotid feeding the anterior part FIG. 2. Schematically illustrate microvasculature blood supply FIG. 3. illustrate perforators with saccular aneurysms FIG. 4. a and b illustrate an ischemic Cerebrovascular Accident FIG. 5. shows a prior art monolayer stent (Wallstent™)
Figure 2:
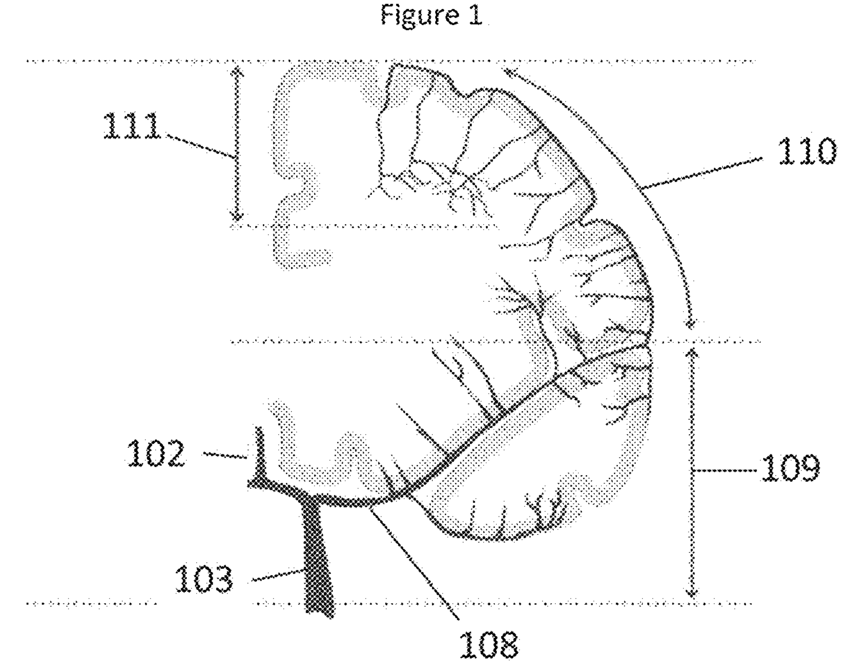
Figure 3:
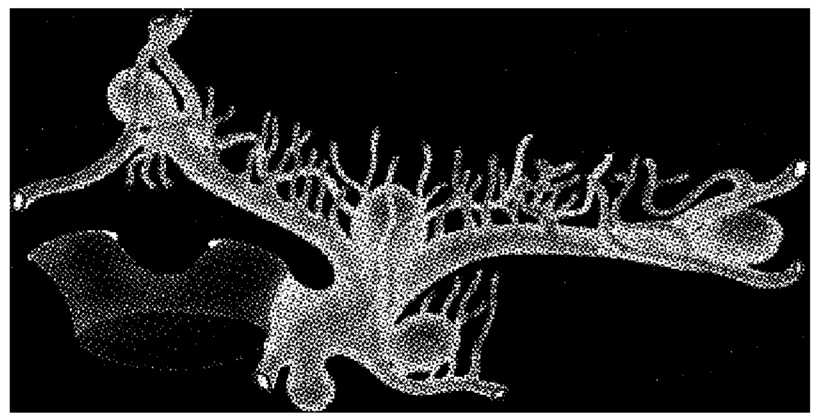
Figure 4:
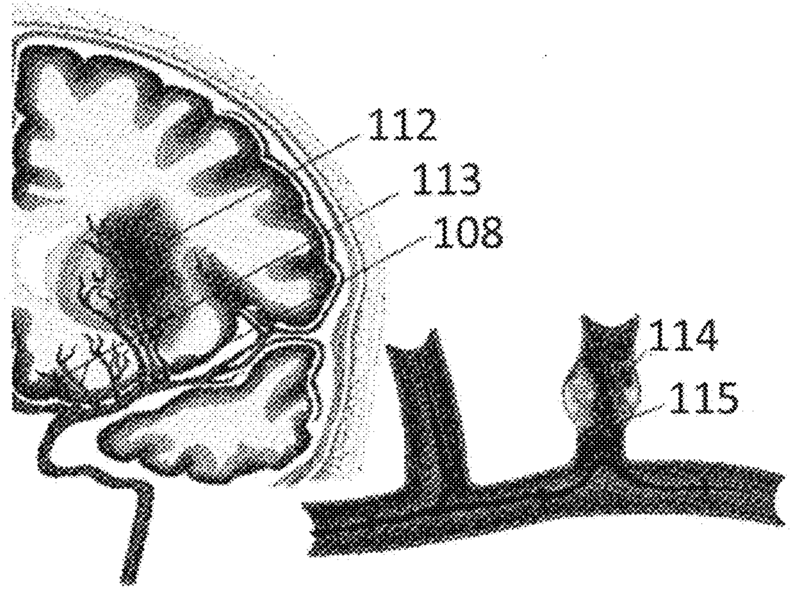
Figure 4:
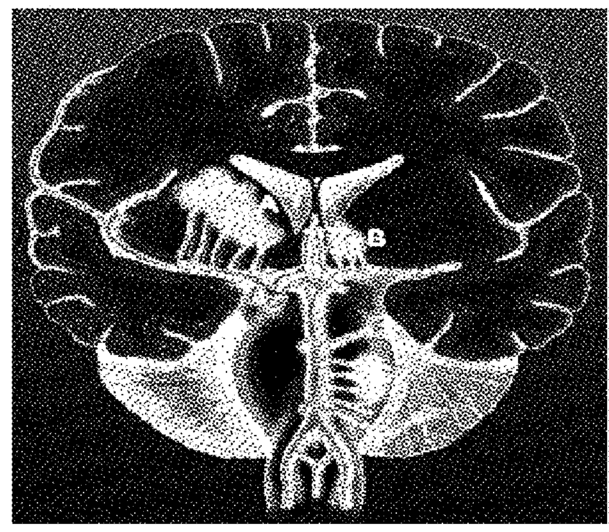
Figure 5:
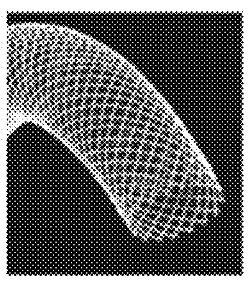

1. Endoluminal implantable prosthesis
2. Main artery wall
3. Side artery
5. Main artery diameter
6. Endoluminal implantable prosthesis lumen axis
7. Outermost layer
8. Intermediate layer
9. Innermost layer
10. line parallel to the lumen axis crossing the outermost layer
11. line parallel to the lumen axis crossing the innermost layer
12. line parallel to the lumen axis crossing the intermediate layer
101. Cerebral Arteries
102. Circle of Willis
103. Internal carotid artery
104. Basilar Artery
105. Vertebral artery
106. External Carotid artery
107. Common Carotid artery
108. Middle cerebral artery
109. Large cerebral arteries
110. Plial Cerebral arteries
111. Penetrating arteriole capillaries
112. Area of ischemia
113. Lenticulostriate perforator
114. Artherosclerotic plaque
115. Blood clot

DETAILED DESCRIPTION

The 3-D Woven Mesh

By adding at least an additional interweaved (interbraided) layer to make 3-D woven mesh, the number of pores increases with more open surface for a given surface area. This means that the flow can occur through both the interwoven and intrawoven regions.

Flow resistance through the mesh is an important property of the mesh geometry, which is characterized by porosity.

The flow crossing through a monolayer layer mesh (as standard stent) has a limited flow rate. In other words, the flow rate through one window of the mesh does not increase beyond the pore capacity that constitutes one element of its porosity. Increase the flow through the window mesh will increase the resistance to the flow passage.

The only way to decrease this resistance is to increase number of pores that can be distributed on a large surface.

The unique possibility to do this over a tubular mesh is to have a volume structure (3D) with different interlocked layers to increase the number of pores. (The overlapped monolayers have less pores distribution because they have no interlocks between to increase the number of pores)

It has been discovered that, contrary to prior art, having an external layer with a higher wire density, and hence a higher surface coverage (i.e. the partial coverage induced by the external layer only) improves the flow and reduce the pressure drop on side vessels jailed with said structure.

Figure 6:
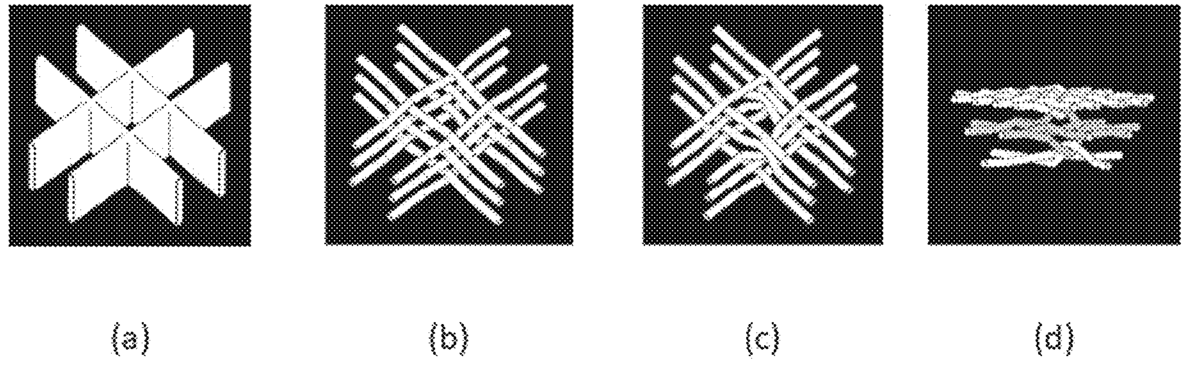
FIG. 6 shows flow restriction types of the examples
Figure 10:
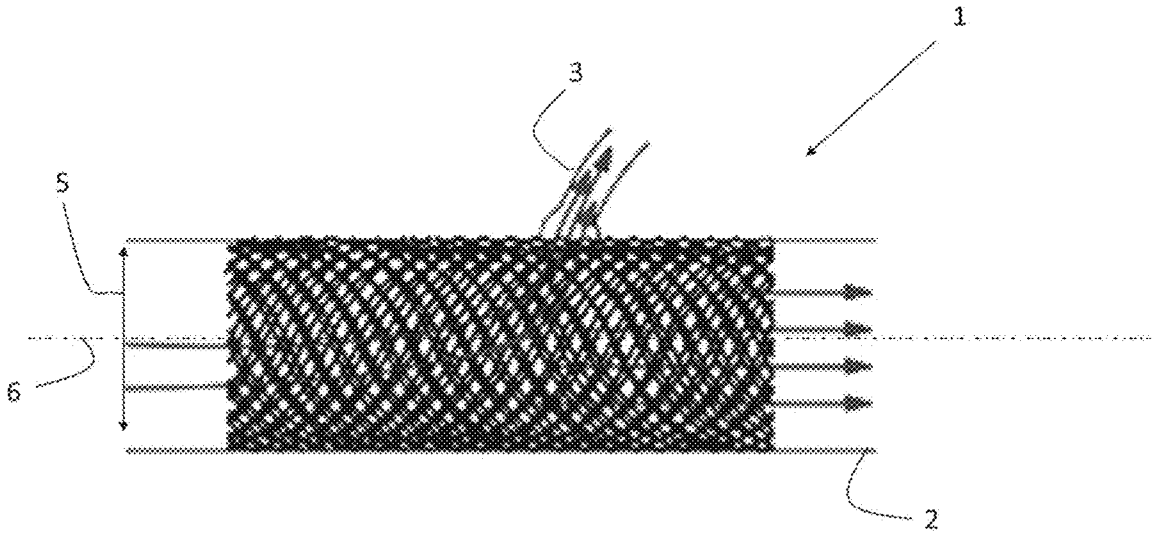
FIG. 10 represents an implanted endoluminal prosthesis according to the present disclosure.

Physical Tests:

Physical permeability test has been conducted to evaluate the flow efficiency with 4 different flow restriction configurations with the same thickness;

Ref: Reference no flow restriction (open system);

(a) 1 monolayer (FIG. 6*a*);

(b) 3 independent packed monolayers, with the same porosity each (i.e. wire density 2/2/2, see FIG. 6*b*);

(c) 3 monolayers interlocked with the same window size of the layers or the same porosity (i.e. wire density 2/2/2, see FIG. 6*c*);

(d) 3 interlaced layers with 3 different degrees of porosity, lower weave (innermost layer) having a low wire density (i.e. low pores density), medium weave with medium pore density (i.e. intermediate wire density) and upper weave (outermost layer) with high pore density (and high wire density), as schematically shown in FIGS. 6(*d*) and 7 to 9 (these last figures corresponding to densities from outside layer to inside layer being multiples of 8/4/2).

The SCR of the endoluminal prosthesis is defined by the relation:

$$SCR=Sw/St$$

Wherein "Sw" is the actual surface covered by wires composed in the endoluminal prosthesis, and "St" is the total surface are of the wall of the endoluminal prosthesis when observed normal with respect to the wall.

SCR of individual layer may for example be determined by determining the three dimensional structure of the stent by micro-CT scan to measure identify empty area and metal-occupied area at each depth level and to convert the result to SRC of each depth level, The same measurement may also be used to estimate the wires density in each layer.

A two-litter container filled with water was connected through a tube to a discharge opening having a 4 mm diameter. The discharge opening was covered successively with the different flow restrictions described hereabove. The time to empty the container was measured three times with each configuration. The standard deviation in each case was less than 1%.

Table one summarize the obtained results.

TABLE 1 flow testing results corresponding to samples represented on FIG. 6

| Type of Flow restriction | Time to empty [sec] | Average Flow rate [ml/sec] | Flow improvement | Total SCR (All layers) |
|---|---|---|---|---|
| Ref. | 11.79 | 170 | — | — |
| (a) | 11.56 | 173 | 1.9% | 32% |
| (b) | 11.47 | 174 | 2.7% | 33% |
| (c) | 11.44 | 175 | 3% | 44% |
| (d) | 10.95 | 183 | 7.1% | 44% |

The different samples were 3D printed mimicking real inter-braided stents. The simulated wires were about 250 μm thick and organized as a squared lattice. The wire density from inside to outside in sample (d) was 4/2/1.

Based on this data the pore distribution of the staged porosity volume lowers the resistance, and consequently enhance the flow. The open surface area induces positive gradient pressure between upstream and downstream of the mesh. In other word the pressure gradient is viewed as the force driving flow where F. ΔP/R (R=resistance opposed by the wire mesh to the flow). If the ΔP (Pressure Drop) the resistance R to the flow decreases.

The decrease of the resistance smoothens the flow crossing the mesh as a laminar flow. This phenomenon enhances the flow perfusion As a small vessel, the perforator has a resistance to the flow, which affects the flow distribution at microcirculation level of the brain tissue, so the pore distribution through the 3D volume of the mesh lowers the coefficient resistance, and consequently increases of flow and ΔP.

As a result, the device design has the ability to strengthen, to stabilize the stream flow through the perforators with minimized head loss.

Figure 11:
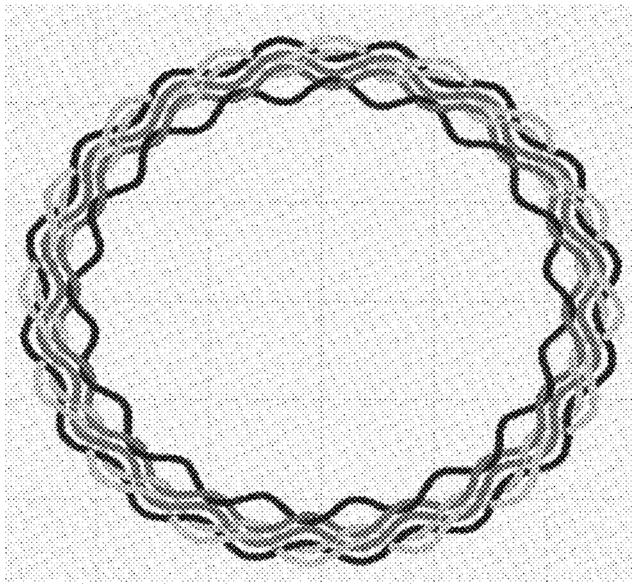
FIG. 11 depicts the top view of a stent made of 96 wires with wire density of 48/32/16 according to the present disclosure.
Figure 12:
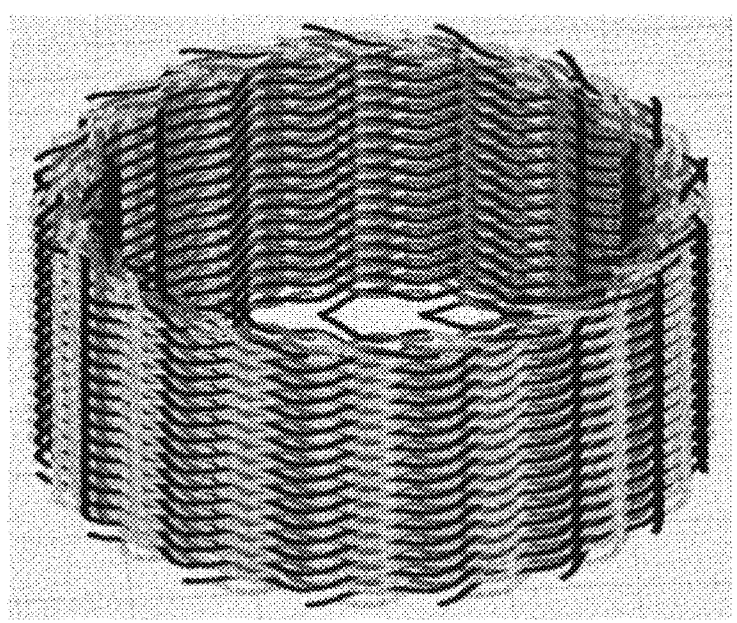
FIG. 12 depicts a prospective view of the stent of FIG. 11.

Table 2 present examples of preferred endoluminal prosthesis according to the present disclosure, the first example (96 wires) corresponding to FIGS. 11 and 12.

TABLE 2

Characteristics of devices made of 96, 102 or 112 wires

| Wire | Device Layers Number of Wires in each layer | | | Wire size | Nominal Diameter | In Artery Diameter | Pitch length | Total Free surface | Total SCR |
|---|---|---|---|---|---|---|---|---|---|
| Total | Outermost | intermediate | innermost | (micron) | (mm) | (mm) | (mm) | area % | % |
| 96 | 48 | 32 | 16 | 35 | 4 | 3 | 11.69 | 59.45 | 40.55 |
| | 48 | 32 | 16 | 35 | 4.5 | 3.5 | 12.74 | 63.71 | 36.29 |
| | 48 | 32 | 16 | 35 | 3.5 | 2.5 | 10.61 | 53.86 | 46.14 |
| 102 | 54 | 32 | 16 | 35 | 4 | 3 | 11.54 | 57.07 | 42.93 |
| | 54 | 32 | 16 | 35 | 4.5 | 3.5 | 12.65 | 61.6 | 38.4 |
| | 54 | 32 | 16 | 35 | 3.5 | 2.5 | 10.61 | 51.15 | 48.85 |

TABLE 2-continued

| Characteristics of devices made of 96, 102 or 112 wires | | | | | | | | | | |
|---|---|---|---|---|---|---|---|---|---|---|
| Wire | Device Layers Number of Wires in each layer | | | Wire size | Nominal Diameter | In Artery Diameter | Pitch length | Total Free surface | Total SCR |
| Total | Outermost | intermediate | innermost | (micron) | (mm) | (mm) | (mm) | area % | % |
| 112 | 64 | 32 | 16 | 35 | 4 | 3 | 11.69 | 53.71 | 46.29 |
| | 64 | 32 | 16 | 35 | 4.5 | 3.5 | 12.74 | 58.46 | 41.54 |
| | 64 | 32 | 16 | 35 | 3.5 | 2.5 | 10.61 | 47.55 | 52.45 |

The invention claimed is:

1. A cerebral implantable endoluminal prosthesis for use in the treatment of cerebral aneurysm involving branches, the prosthesis having a multilayer configuration comprising:

at least one self-expandable braided framework extending along an axis configured to expand from a radially compressed state in a delivery configuration to a radially expanded state;

the self-expandable braided framework being formed by wires and devoid of any impermeable cover layer;

wherein the self-expandable braided framework comprises a plurality of layers of wires made of biocompatible material, and forms a wall of the endoluminal prosthesis, each of the layers of wires forming a mesh, the meshes forming a lattice with a plurality of the wires of the layers, the meshes being interlocked, the wires being integrated in the mesh of at least one adjacent layer;

wherein the plurality of layers of wires includes an intermediate layer located between an innermost layer and an outermost layer;

wherein the self-expandable braided framework further comprises a lumen in a cylindrical form having a circular cross-section, an axis, and a constant diameter;

wherein a number of wires crossing a line parallel to the lumen axis in a given layer is higher in the outermost layer than in the innermost layer; and wherein the number of wires in the intermediate layer is comprised between the number of wires in the outermost layer and the number of wires in the innermost layer.

2. The cerebral implantable endoluminal prosthesis according to claim 1 wherein a ratio of the number of wires in the outermost layer to the innermost layer is at least 1.5.

3. The cerebral implantable endoluminal prosthesis according to claim 1, wherein the number of wires forming the endoluminal prosthesis is comprised between 50 and 120.

4. The cerebral implantable endoluminal prosthesis according to claim 1, having a nominal diameter comprised between 3 and 5.5 mm.

5. The cerebral implantable endoluminal prosthesis according to claim 1, wherein the wires forming the endoluminal prosthesis have a diameter comprised between 10 and 70 μm.

6. The cerebral implantable endoluminal prosthesis according to claim 1, wherein a ratio of a surface coverage ratio of the outer layer to a surface coverage ratio of the inner layer is at least 1.5.

7. The cerebral implantable endoluminal prosthesis according to claim 1, wherein the biocompatible material is a metallic substrate selected from the group consisting of titanium, a nickel-titanium alloy, a stainless steel, and a cobalt-chromium-nickel alloy.

8. The cerebral implantable endoluminal prosthesis according to claim 1 wherein a ratio of the number of wires in the outermost layer to the innermost layer is at least 2.

9. The cerebral implantable endoluminal prosthesis according to claim 1, wherein the number of wires forming the endoluminal prosthesis is comprised between 80 and 102.

10. The cerebral implantable endoluminal prosthesis according to claim 1, wherein the number of wires forming the endoluminal prosthesis is less than 100.

11. The cerebral implantable endoluminal prosthesis according to claim 1, wherein the wires forming the endoluminal prosthesis have a diameter comprised between 20 and 50 μm.

12. The cerebral implantable endoluminal prosthesis according to claim 1, wherein the wires forming the endoluminal prosthesis have a diameter comprised between 30 and 40 μm.

* * * * *